United States Patent
Yamaga et al.

(10) Patent No.: US 10,918,293 B2
(45) Date of Patent: Feb. 16, 2021

(54) MAGNETIC MEASURING APPARATUS

(71) Applicants: Takumi Yamaga, Kanagawa (JP); Hiroshi Deguchi, Kanagawa (JP); Koji Yamaguchi, Kanagawa (JP); Takafumi Ishibe, Osaka (JP); Shunichi Matsumoto, Kanagawa (JP); Shigenori Kawabata, Tokyo (JP); Shuta Ushio, Tokyo (JP)

(72) Inventors: Takumi Yamaga, Kanagawa (JP); Hiroshi Deguchi, Kanagawa (JP); Koji Yamaguchi, Kanagawa (JP); Takafumi Ishibe, Osaka (JP); Shunichi Matsumoto, Kanagawa (JP); Shigenori Kawabata, Tokyo (JP); Shuta Ushio, Tokyo (JP)

(73) Assignees: Ricoh Company, Ltd., Tokyo (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 384 days.

(21) Appl. No.: 16/116,148

(22) Filed: Aug. 29, 2018

(65) Prior Publication Data
US 2019/0059758 A1    Feb. 28, 2019

Related U.S. Application Data

(63) Continuation of application No. PCT/JP2017/005824, filed on Feb. 17, 2017.

(30) Foreign Application Priority Data

Mar. 3, 2016 (JP) ................................ 2016-041406

(51) Int. Cl.
  *G01R 33/035* (2006.01)
  *A61B 5/05* (2006.01)
  (Continued)

(52) U.S. Cl.
  CPC ........ *A61B 5/04005* (2013.01); *A61B 5/0035* (2013.01); *A61B 5/05* (2013.01);
  (Continued)

(58) Field of Classification Search
  CPC ..... A61B 5/0035; A61B 5/04005; A61B 5/05; A61B 5/4041; A61B 5/704; A61B 6/045;
  (Continued)

(56) References Cited

U.S. PATENT DOCUMENTS 4,996,479 A    2/1991  Hoenig
5,302,831 A *  4/1994  Gallagher ............. H01J 37/244
                                                   250/370.15

(Continued)

FOREIGN PATENT DOCUMENTS

JP    H02-114941    4/1990
JP    H06-007313    1/1994
(Continued)

OTHER PUBLICATIONS

Adachi et al., "A SQUID System for Measurement of Spinal Cord Evoked Field of Supine Subjects", IEEE Transaction on Applied Superconductivity, vol. 19, No. 3 Jun. 2009, pp. 861-866. (Year: 2009).*

(Continued)

*Primary Examiner* — Boniface N Nganga
(74) *Attorney, Agent, or Firm* — IPUSA, PLLC

(57) ABSTRACT

A magnetic measuring apparatus includes an inclination gantry including a mount surface and an inclined surface that is inclined with respect to the mount surface, a cryostat disposed on the inclined surface, a cryocooling system (Continued)

connected to the cryostat, a sensor tube connected to the cryostat and including a curved surface that does not curve in a predetermined direction and curves in a direction orthogonal to the predetermined direction such that a center of the curved surface protrudes with respect to side edges of the curved surface, and a magnetic sensor that measures biomagnetism and is housed in the sensor tube such that a sensor surface of the magnetic sensor faces the curved surface. The sensor surface is inclined with respect to the mount surface in a direction that is the same as a direction in which the inclined surface is inclined.

10 Claims, 7 Drawing Sheets

(51) Int. Cl.
  *A61B 5/04* (2006.01)
  *A61B 5/00* (2006.01)
  *A61B 6/04* (2006.01)
  *A61B 6/00* (2006.01)
  *G01R 33/00* (2006.01)
  *A61N 1/04* (2006.01)

(52) U.S. Cl.
  CPC ............ *A61B 5/4041* (2013.01); *A61B 5/704* (2013.01); *A61B 6/045* (2013.01); *A61B 6/5247* (2013.01); *G01R 33/0082* (2013.01); *G01R 33/035* (2013.01); *A61B 2562/0223* (2013.01); *A61B 2562/164* (2013.01); *A61N 1/0456* (2013.01)

(58) Field of Classification Search
  CPC .......... A61B 6/5247; A61B 2562/0223; A61B 2562/164; G01R 33/035; G01R 33/0082; A61N 1/0456
  See application file for complete search history.

(56) References Cited

U.S. PATENT DOCUMENTS

| | | | |
|---|---|---|---|
| 5,343,707 A | 9/1994 | Sata | |
| 6,275,719 B1* | 8/2001 | Kandori | A61B 5/04007 324/248 |
| 8,481,995 B2 | 7/2013 | Yamaga | |
| 8,583,208 B2 | 11/2013 | Adachi et al. | |
| 8,711,297 B2 | 4/2014 | Matsuoka et al. | |
| 8,847,394 B2 | 9/2014 | Onodera et al. | |
| 2002/0019589 A1 | 2/2002 | Tsukada et al. | |
| 2002/0050815 A1* | 5/2002 | Suzuki | G01R 33/24 324/248 |
| 2006/0055402 A1* | 3/2006 | Seki | A61B 5/04007 324/262 |
| 2010/0279460 A1 | 11/2010 | Yamaga et al. | |
| 2013/0014528 A1* | 1/2013 | Stabacinskiene | G01N 23/20033 62/129 |
| 2014/0212705 A1 | 7/2014 | Horiuchi et al. | |
| 2015/0323618 A1* | 11/2015 | Merfeld | G01R 33/3804 324/321 |
| 2017/0168121 A1* | 6/2017 | Yu | G01R 33/007 |

FOREIGN PATENT DOCUMENTS

| | | |
|---|---|---|
| JP | 2000-041965 | 2/2000 |
| JP | 2002-136493 | 5/2002 |
| JP | 2002-136494 | 5/2002 |
| JP | 2003-304851 | 10/2003 |
| JP | 4013492 | 11/2007 |
| JP | 4034429 | 1/2008 |
| JP | 2008-206809 | 9/2008 |
| JP | 4397276 | 1/2010 |
| JP | 4834076 | 12/2011 |
| JP | 2012-020143 | 2/2012 |
| JP | 5137149 | 2/2013 |
| JP | 2017-015620 | 1/2017 |

OTHER PUBLICATIONS

Korber et al., "SQUIDs in biomagnetism: a roadmap towards improved healthcare", Supercond. Sci Technol. 20 (2016) 113001, 30 pages. (Year: 2016).*

Sumiya et al., "Magnetospinography visualizes electrophysiological activity in the cervical spinal cord", Scientific Reports 7: 2192, 12 pages, published online May 19, 2017. (Year: 2017).*

Adachi et al., "Recent advancements in the SQUID magnetospinogram system", Supercond. Sci. Technol. 30 (2017) 063001, 16 pages. (Year: 2017).*

Adachi Y et al: "A SQUID biomagnetometer system for measurement of a human cervical spinal cord evoked field; A SQUID biomagnetometer system for measurement of a human cervical spinal cord evoked field", Superconductor Science and Technology, IOP Publishing, Techno House, Bristol, GB, vol. 18, No. 12, Dec. 1, 2005 (Dec. 1, 2005), pp. S303-S307, XP020088038, ISSN: 0953-2048, DOI : 10.1088/0953-2048/18/12/013 *abstract* *p. 304, left-hand column, line 23-p. 306, left-hand column, line 15*.

Extended European Search Report for 17759677.2 dated Feb. 20, 2019.

International Search Report dated May 16, 2017 in PCT Application No. PCT/JP2017/005824 filed on Feb. 17, 2017.

* cited by examiner

MAGNETIC MEASURING APPARATUS

CROSS-REFERENCE TO RELATED APPLICATIONS

The present application is a continuation application filed under 35 U.S.C. 111(a) claiming benefit under 35 U.S.C. 120 and 365(c) of PCT International Application No. PCT/JP2017/005824, filed on Feb. 17, 2017, which is based on and claims the benefit of priority of Japanese Patent Application No. 2016-041406 filed on Mar. 3, 2016, the entire contents of which are incorporated herein by reference.

BACKGROUND OF THE INVENTION

1. Field of the Invention

An aspect of this disclosure relates to a magnetic measuring apparatus.

2. Description of the Related Art

There is a known magnetic measuring apparatus including a sensor array that is composed of multiple superconducting magnetic sensors arranged in rows and columns and is disposed on the inner surface of an end portion of a sensor tube (see, for example, Japanese Patent No. 4397276).

An end face of the sensor tube of the magnetic measuring apparatus is brought into contact with a living body to measure the biomagnetism with the magnetic sensors disposed in the sensor tube. The measurement is repeated while causing the subject to move relative to the sensor tube. However, because the mobility of the spine of an elderly person is reduced due to aging, an elderly person cannot freely bend the cervical region and the lumbar region. If the cervical region or the lumbar region of a subject is in a natural state, the center of the end face of the sensor tube is positioned away from the cervical region or the lumbar region of the subject and it becomes difficult to properly measure the biomagnetism. Also, if the cervical region or the lumbar region is bent by force, the magnetic field generated by the movement of muscles becomes a noise source and the biomagnetism is not properly measured.

A disclosed technology tries to solve these problems (see, for example, Japanese Patent No. 4834076). In the disclosed technology, the end face of a sensor tube curves smoothly such that the center of the sensor tube protrudes in a given direction with respect to the upper and lower edges. This configuration makes it easier to bring the end face of the sensor tube into contact with the cervical region and the lumbar region of a subject without requiring the subject to bend the cervical region and the lumbar region, and thereby makes it possible to measure weak magnetism generated in a spinal cord and a spinal nerve.

However, because the shapes of the cervical region and the lumbar region vary greatly depending on the age and the physical constitution of a subject, there are many cases where the curved shape of the sensor tube does not properly fit the cervical region and the lumbar region of a subject. In such cases, a gap is formed between the subject and the curved end face, a distance between magnetic sensors and the spinal cord becomes large, and it becomes difficult to detect signals. Accordingly, it is necessary to further improve the sensor tube with the curved end face to suit a larger number of subjects.

For optimal fitting, a swing mechanism for adjusting the inclination of the sensor tube may be added to the magnetic measuring apparatus. However, adding a swing mechanism greatly increases the costs of the magnetic measuring apparatus, may reduce the stability, and may increase vibration noise generated during the measurement of biomagnetism. Also, adding a swing mechanism to the magnetic measuring apparatus makes it impossible to connect the magnetic measuring apparatus to a cryocooling system having a function to recondense vaporized helium into liquid.

As described above, it is extremely difficult to enable a magnetic measuring apparatus to be connected to a cryocooling system while improving the signal detection rate. Also, inclination may be adjusted by using an inclination adjusting mechanism of a bed. However, to improve the fitting of a magnetic measuring apparatus, the bed needs to be inclined in a direction to lower the head of a subject. Accordingly, this approach may place the subject at risk and is not realistic.

SUMMARY OF THE INVENTION

An aspect of this disclosure provides a magnetic measuring apparatus that includes an inclination gantry including a mount surface and an inclined surface that is inclined with respect to the mount surface, a cryostat disposed on the inclined surface, a cryocooling system connected to the cryostat, a sensor tube connected to the cryostat and including a curved surface that does not curve in a predetermined direction and curves in a direction orthogonal to the predetermined direction such that a center of the curved surface protrudes with respect to side edges of the curved surface, and a magnetic sensor that measures biomagnetism and is housed in the sensor tube such that a sensor surface of the magnetic sensor faces the curved surface. The sensor surface is inclined with respect to the mount surface in a direction that is the same as a direction in which the inclined surface is inclined.

DESCRIPTION OF THE EMBODIMENTS

An aspect of this disclosure makes it possible to provide a magnetic measuring apparatus that has an improved signal detection rate and can be connected to a cryocooling system.

Embodiments of the present invention are described below with reference to the accompanying drawings. Throughout the accompanying drawings, the same reference number is assigned to the same component, and repeated descriptions of the component may be omitted.

Figure 1A:
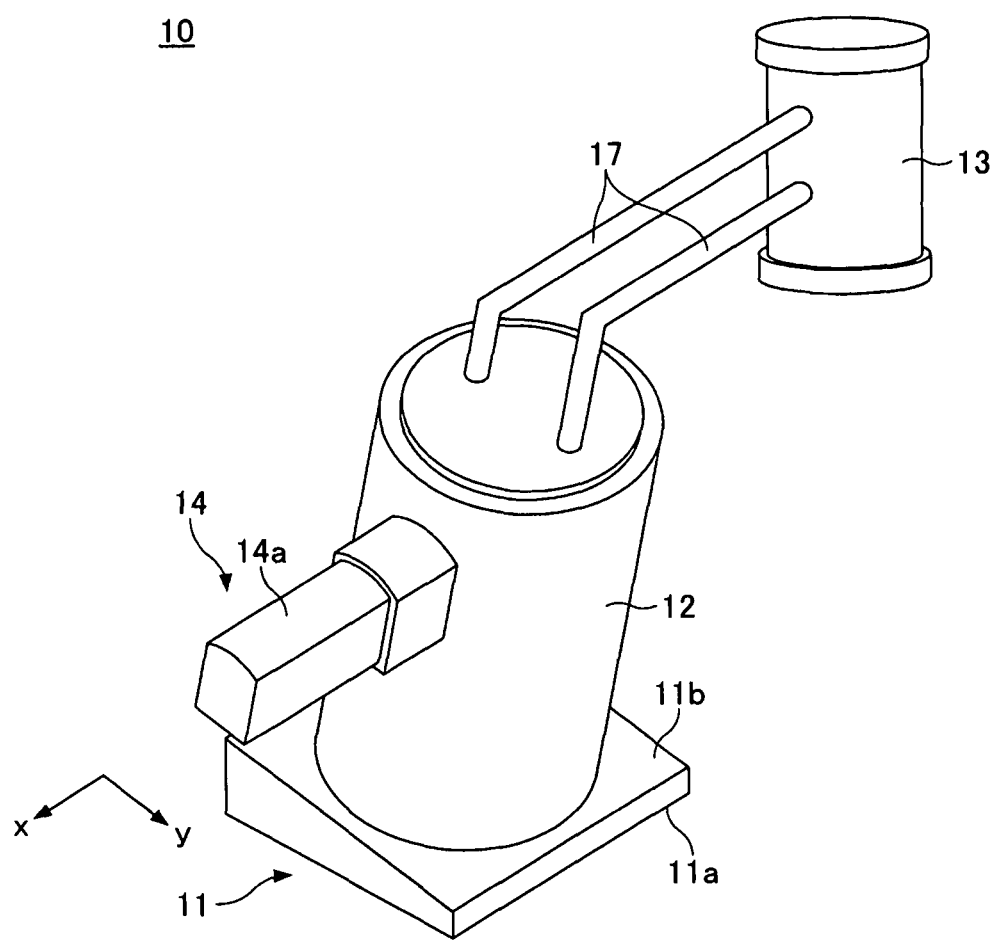
FIG. 1A is a perspective view exemplifying a magnetic measuring apparatus according to an embodiment.
Figure 1B:
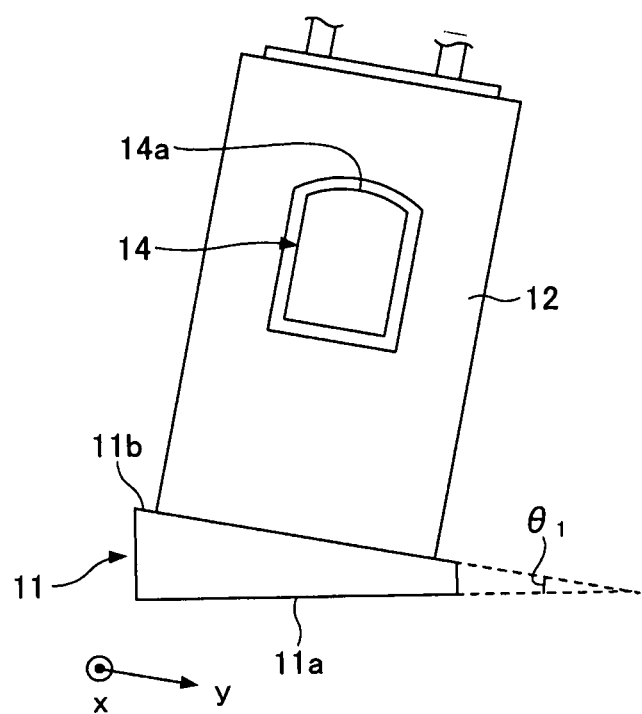
FIG. 1B is a side view exemplifying a magnetic measuring apparatus according to an embodiment.
Figure 2:
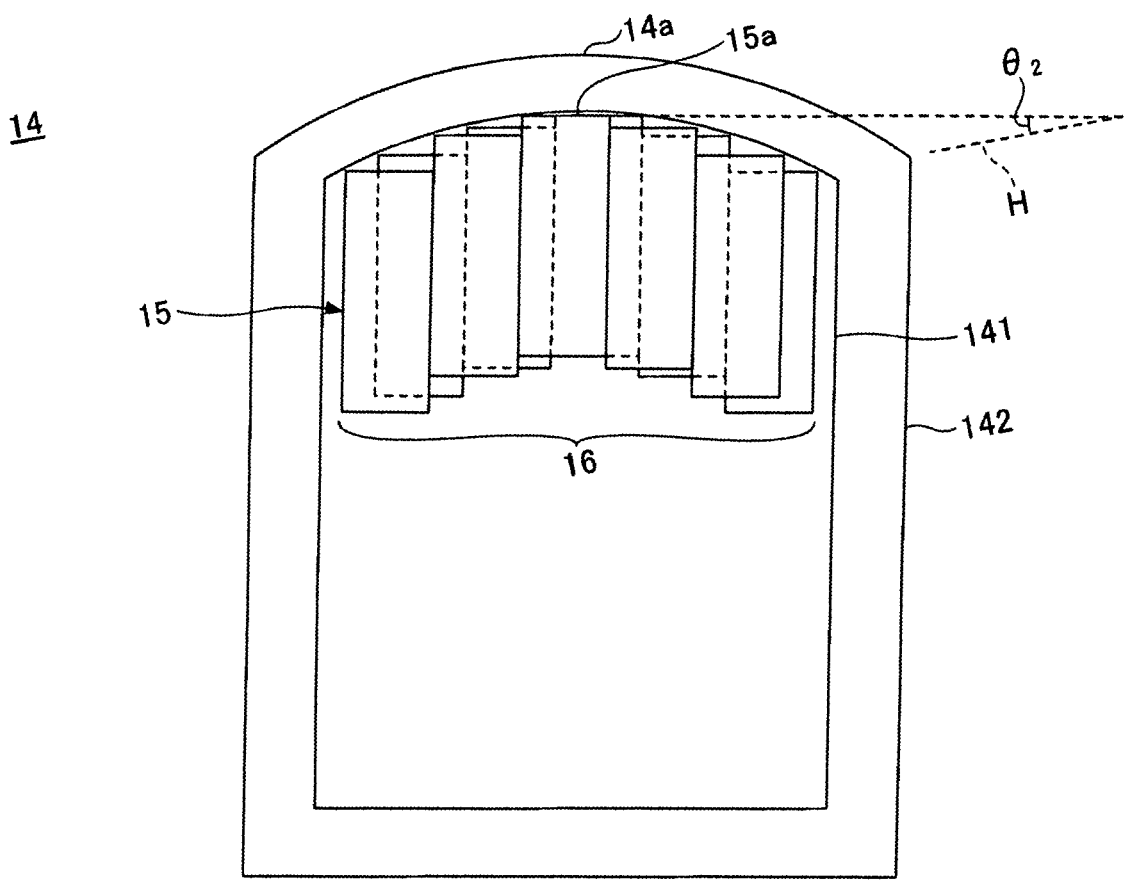
FIG. 2 is a cross-sectional view exemplifying the inside of a sensor tube of a magnetic measuring apparatus according to an embodiment.

FIG. 1A is a perspective view exemplifying a magnetic measuring apparatus according to an embodiment. FIG. 1B is a side view exemplifying the magnetic measuring apparatus according to the embodiment. FIG. 2 is a cross-sectional view exemplifying the inside of a sensor tube of the magnetic measuring apparatus according to the embodiment.

As illustrated in FIGS. 1A, 1B, and 2, a magnetic measuring apparatus 10 can properly measure weak magnetism generated by a living body and includes an inclination gantry 11, a cryostat 12, a cryocooling system 13, and a sensor tube 14. A magnetic sensor array 16 composed of multiple magnetic sensors 15 is housed in the sensor tube 14. The magnetic measuring apparatus 10 is described in detail below.

The inclination gantry 11 includes a mount surface 11a and an inclined surface 11b that is inclined with respect to the mount surface 11a. The mount surface 11a is a flat surface that contacts, for example, a floor surface of a place where the magnetic measuring apparatus 10 is used. The inclined surface 11b is a flat surface on which the cryostat 12 is disposed. An inclination angle $\theta_1$ (which is hereafter simply referred to as the "inclination angle $\theta_1$") of the inclined surface 11b with respect to the mount surface 11a is a fixed value, and no adjusting mechanism is provided to adjust the inclination angle $\theta_1$. The inclination angle $\theta_1$ can be set at any appropriate value. For example, the inclination angle $\theta_1$ is greater than or equal to about 10 degrees and less than or equal to about 20 degrees.

The cryostat 12 is disposed on the inclined surface 11b of the inclination gantry 11. The cryostat 12 is also referred to as a "dewar", and contains liquid helium that is necessary for cryogenic operations of the magnetic sensor array 16 that detects a magnetic field generated by a living body.

The cryocooling system 13 recondenses vaporized helium into liquid, and is connected via flow channels 17 to the cryostat 12.

The sensor tube 14 is a part that contacts a subject, and is connected to the cryostat 12. In this example, the sensor tube 14 protrudes horizontally from a side surface of the cryostat 12. However, the present invention is not limited to this example.

The sensor tube 14 includes a curved surface 14a that does not curve in a predetermined direction (which is hereafter referred to as an "x direction") and curves in a direction (which is hereafter referred to as a "y direction") orthogonal to the predetermined direction such that the center of the curved surface 14a protrudes with respect to the side edges The width of the sensor tube 14 in the y direction is, for example, greater than or equal to about 5 cm and less than or equal to about 20 cm. For example, the curved surface 14a smoothly curves in the y direction such that the center of the curved surface 14a protrudes by a distance greater than or equal to 0.5 cm and less than or equal to 4 cm with respect to the side edges of the curved surface 14a.

The sensor tube 14 includes an inner vessel 141 and an outer vessel 142, and the magnetic sensor array 16 is housed in the inner vessel 141. The magnetic sensor array 16 is composed of multiple magnetic sensors 15 that are arranged such that sensor surfaces 15a of the magnetic sensors 15 face the curved surface 14a. For example, multiple magnetic sensors 15 are arranged in a row in the y direction and multiple rows of the magnetic sensors 15 are arranged in the x direction.

In this case, the positions of the magnetic sensors 15 in rows that are adjacent to each other in the x direction may be shifted in the y directions. For example, assume a case where five magnetic sensors 15 are arranged at a pitch p (e.g., 20 mm) in the y direction to form one sensor row, and multiple sensor rows are arranged at a pit w (e.g., 20 mm) in the x direction. In this case, the positions of the magnetic sensors 15 in sensor rows that are adjacent to each other in the x direction may be shifted by p/2 in the y direction.

Also, the magnetic sensors 15 may be arranged such that the sensor surface 15a of one of the magnetic sensors 15 whose positon in the sensor tube 14 is closer to the center of the curved surface 14a in the y direction protrudes more toward the curved surface 14a compared with the sensor surface 15a of another one of the magnetic sensors 15 that is positioned closer to a side edge of the curved surface 14a. This arrangement makes it possible to reduce the distances between the sensor surfaces 15a of the magnetic sensors 15 and an examination region.

In the magnetic measuring apparatus 10, the sensor tube 14 is connected (or fixed) to the cryostat 12. Accordingly, when the cryostat 12 is placed on the inclined surface lib of the inclination gantry 11, the sensor surface 15a of each of the magnetic sensors 15 housed in the sensor tube 14 is inclined along with the sensor tube 14 with respect to the mount surface 11a of the inclination gantry 11 in the same direction as the inclined surface 11b.

An inclination angle $\theta_2$ (which is hereafter simply referred to as the "inclination angle $\theta_2$") of the sensor surface 15a of each of the magnetic sensors 15 with respect to the mount surface 11a of the inclination gantry 11 is, for example, made equal to the inclination angle $\theta_1$. The inclination angle $\theta_2$ is a fixed value, and no adjusting mechanism is provided to adjust the inclination angle $\theta_2$. The inclination angle $\theta_2$ can be set at any appropriate value, and is preferably greater than or equal to 10 degrees and less than or equal to 20 degrees. In FIG. 2, H indicates a plane that is parallel to the mount surface 11a.

Figure 3:
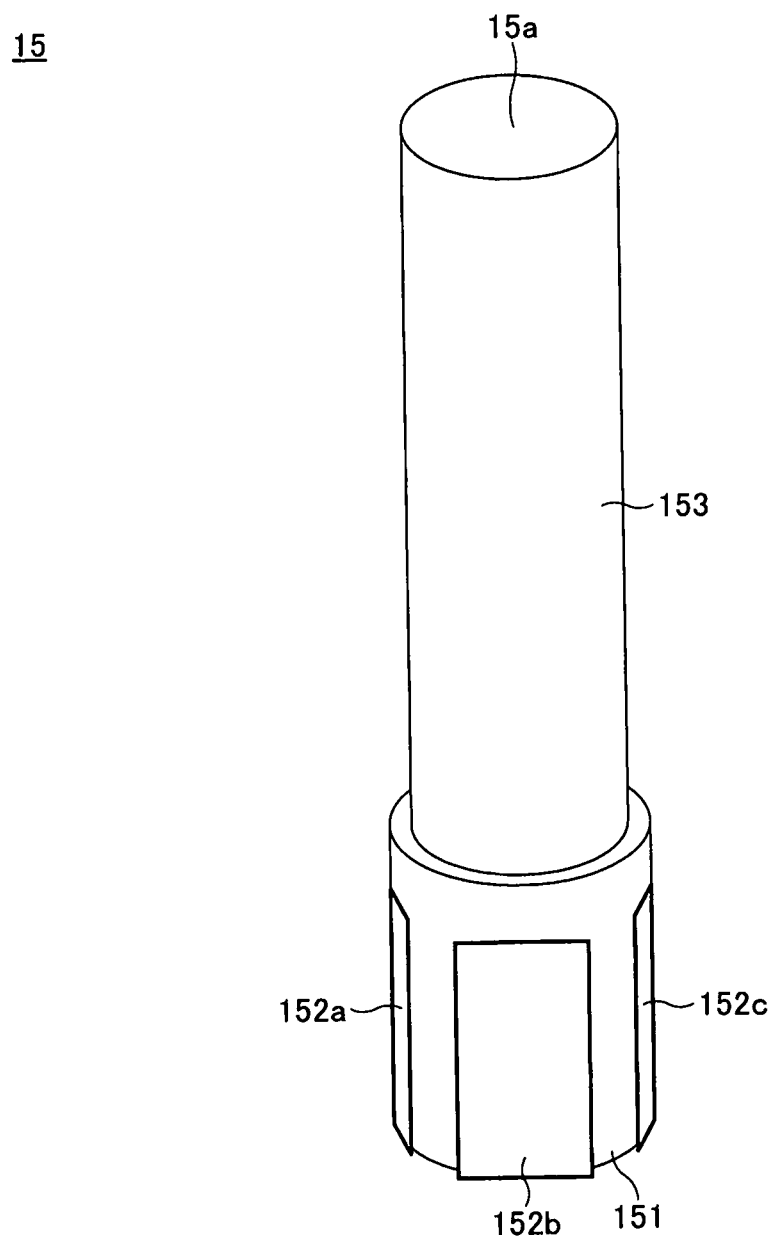
FIG. 3 is a perspective view exemplifying a magnetic sensor of a magnetic measuring apparatus according to an embodiment.

FIG. 3 is a perspective view exemplifying a magnetic sensor of a magnetic measuring apparatus according to an embodiment. The magnetic sensor 15 is a superconducting magnetic sensor for measuring biomagnetism and is, for example, a SQUID sensor. SQUID stands for a superconducting quantum interference device.

The magnetic sensor 15 is a cylindrical sensor including a glass-epoxy cylindrical block 151 in which a SQUID 152a, a SQUID 152b, and a SQUID 152c are disposed and a cylindrical block 153 that is connected to the cylindrical block 151 and includes pick-up coils for the SQUIDs. The upper surface of the cylindrical block 153 is the sensor surface 15a. The diameter of the sensor surface 15a is, for example, about 20 mm.

Figure 4:
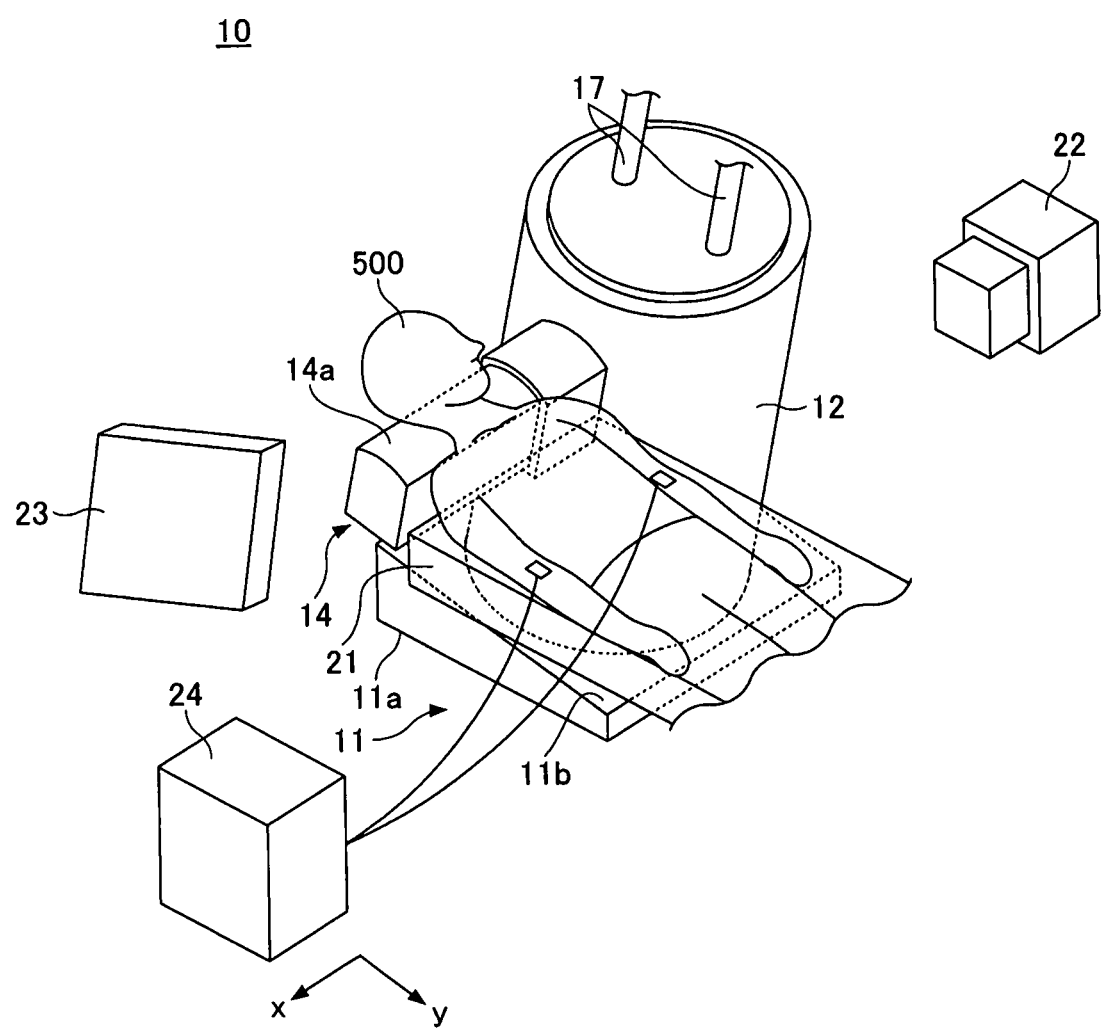
FIG. 4 is a drawing illustrating biomagnetism measurement using a magnetic measuring apparatus according to an embodiment.

FIG. 4 is a drawing illustrating biomagnetism measurement using a magnetic measuring apparatus according to an embodiment. Referring to FIG. 4, the magnetic measuring apparatus 10 includes a bed 21, an X-ray source 22, an X-ray photography film 23, and an electrical stimulation device 24.

The bed 21 is a nonmagnetic bed on which a subject 500 is laid down such that an examination region of the subject 500 contacts the curved surface 14a of the sensor tube 14. The X-ray source 22 and the X-ray photography film 23 constitute an X-ray photography unit that takes an X-ray photograph of a space including a space above the curved surface 14a of the sensor tube 14 in the x direction. The electrical stimulation device 24 electrically and percutaneously stimulates target nerves of the subject 500.

In biomagnetism measurement, electric stimulation is applied to the subject 500 using the electrical stimulation device 24, and the propagation of neural activity synchronized with the electric stimulation is measured by the magnetic sensor array 16. Biomagnetism measurement is preferably conducted in a magnetically shielded room, and the X-ray source 22 and the X-ray photography film 23, which generate magnetic noise, are preferably moved outside of the magnetically shielded room during the measurement. However, this is not essential if no magnetic noise is generated. The cryocooling system 13 and the electrical stimulation device 24 are placed outside of the magnetically shielded room.

The bed 21 preferably includes an inclination adjusting mechanism that can adjust the angle of the bed 21 only in a direction to reduce the angle of the examination region of the subject 500 with respect to the sensor surfaces 15a of the magnetic sensors 15. Even if such an inclination adjusting mechanism is added to the bed 21, the angle of the bed 21 is not adjustable in a direction to lower the head of the subject 500 and therefore the subject 500 is not placed at risk.

As described above, the inclination angle $\theta_2$ is preferably greater than or equal to 10 degrees and less than or equal to 20 degrees. When the upper surface of the bed 21 is horizontal (or parallel to the mount surface 11a), the inclination angle $\theta_2$ becomes equal to an angle formed between the examination region of the subject 500 and the sensor surfaces 15a of the magnetic sensors 15 in the head-and-foot direction of the subject 500.

However, when the magnetic measuring apparatus 10 is used as a magnetocardiograph, the angle formed between the examination region of the subject 500 and the sensor surfaces 15a of the magnetic sensors 15 is preferably about 0 degrees. For example, when the inclination angle $\theta_2$ is 15 degrees, the angle between the examination region of the subject 500 and the sensor surfaces 15a of the magnetic sensors 15 can be set at about 0 degrees by lifting the head side by adjusting the angle of the bed 21 to −15 degrees using the inclination adjusting mechanism. The inclination adjusting mechanism is not necessarily configured to incline the entire bed 21, and may be configured to lift, for example, only the upper body.

Figure 5:
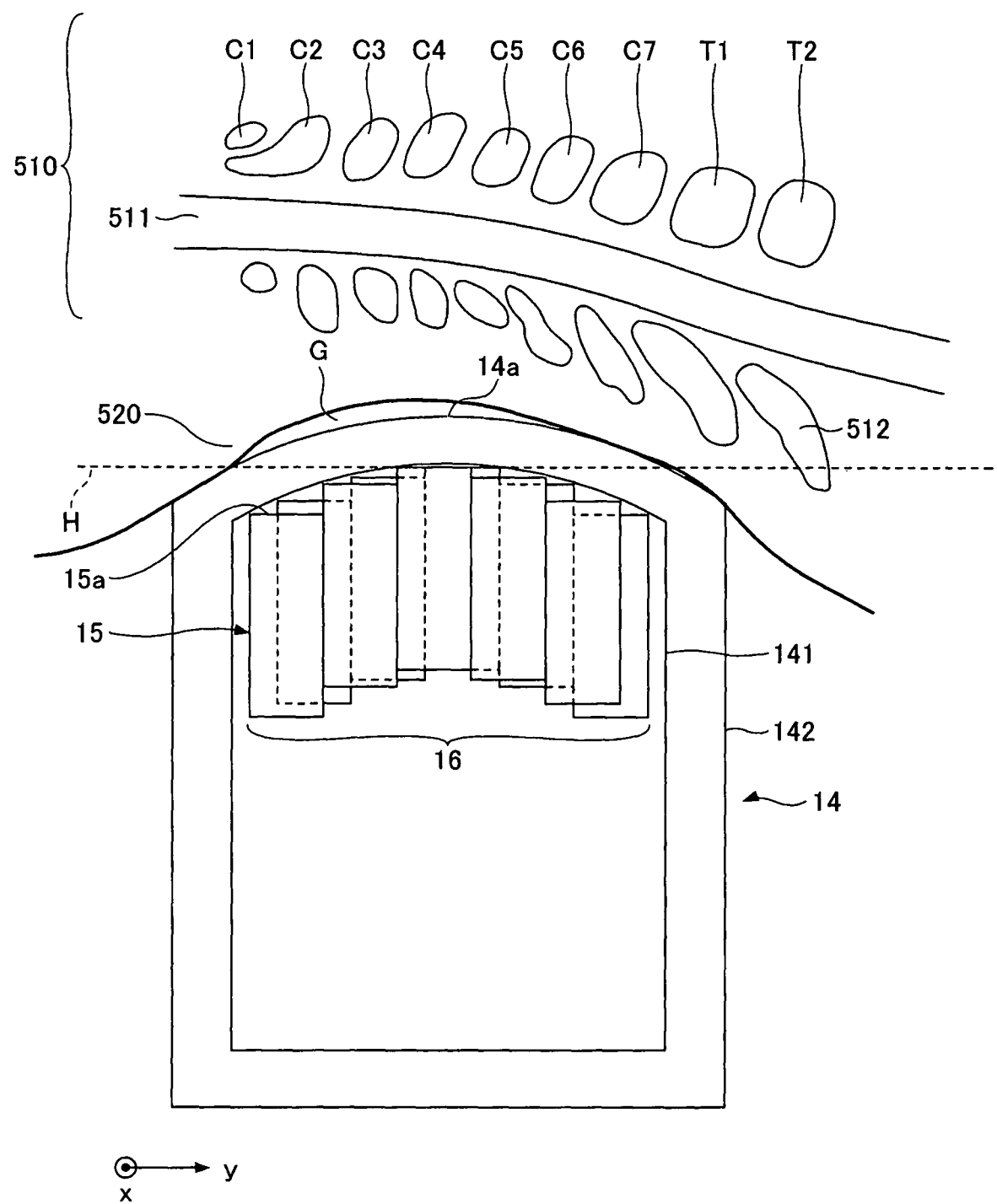
FIG. 5 is a cross-sectional view illustrating a relationship between a cervical region and a sensor tube in biomagnetism measurement according to a comparative example.
Figure 6:
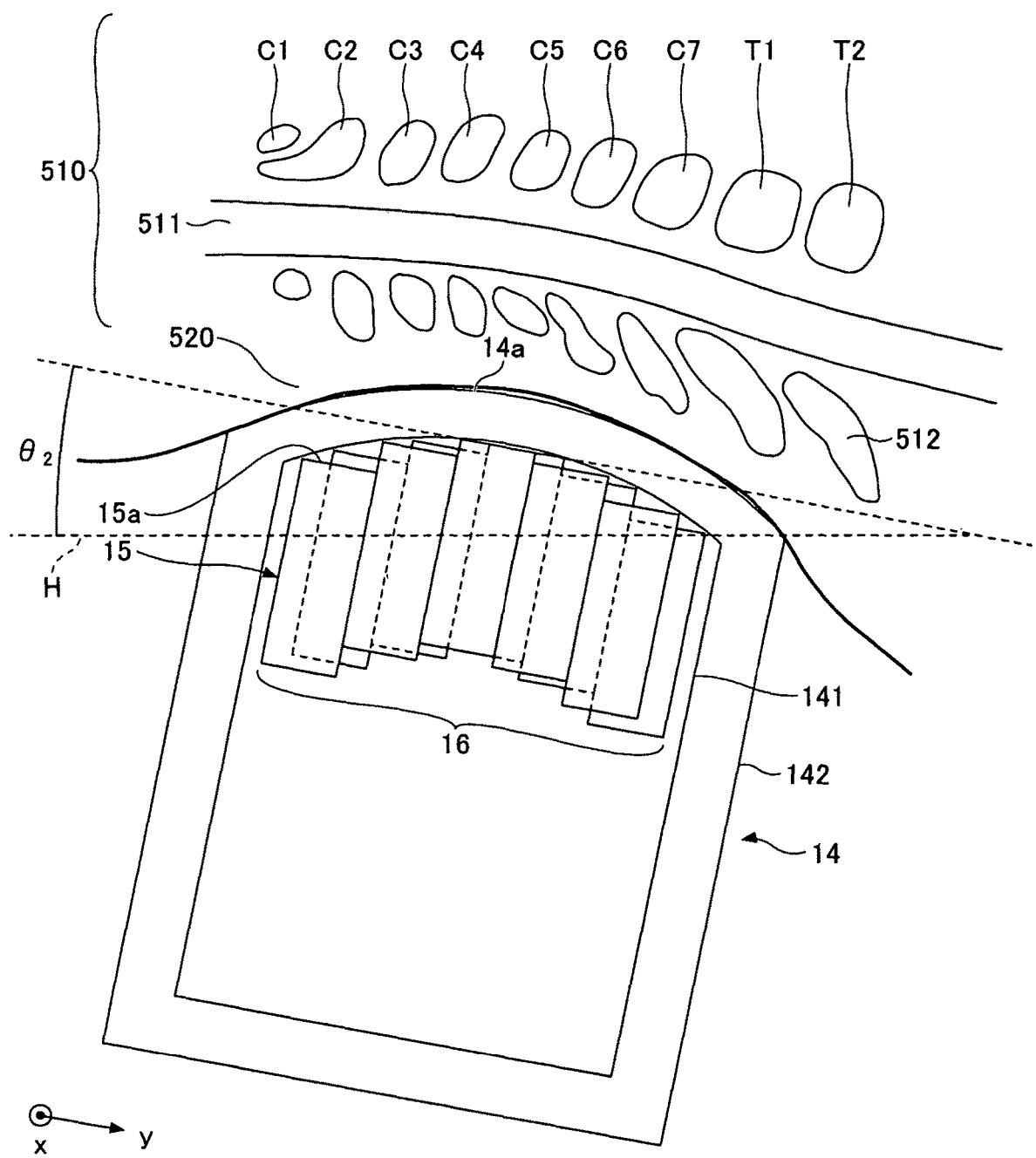
FIG. 6 is a cross-sectional view illustrating a relationship between a cervical region and a sensor tube in biomagnetism measurement according to an embodiment.

FIG. 5 is a cross-sectional view illustrating a relationship between a cervical region and a sensor tube in biomagnetism measurement according to a comparative example. FIG. 6 is a cross-sectional view illustrating a relationship between a cervical region and a sensor tube in biomagnetism measurement according to the present embodiment. The cervical region is an example of an examination region of the subject 500.

In FIGS. 5 and 6, 510 indicates a cervical region. In the cervical region 510, 511 indicates a spinal cord, C1 through C7 indicate first through seventh cervical spines, and T1 and T2 indicate first and second thoracic spines. Spinous processes 512 of the first through seventh cervical spines C1 through C7 and the first and second thoracic spines T1 and T2 are located closer to the sensor tube 14. Also, 520 indicates an occipital protuberance. Further, H indicates a plane that is parallel to the mount surface 11a.

In FIG. 5, an inclination angle of the sensor surface 15a of each of the magnetic sensors 15 with respect to the mount surface 11a of the inclination gantry 11 is about 0 degrees, and the sensor tube 14 is not inclined with respect to the plane H. With this configuration, when the cervical region 510 is stiff and the range of motion of the cervical region 510 is small, a gap G is formed between the sensor tube 14 and the cervical region 510, and the distance between the spinal cord 511 and the sensor surfaces 15a of the magnetic sensors 15 increases.

Assuming that the center of the magnetic sensor array 16 is aligned with the fifth cervical spine C5, parts of the curved surface 14a of the sensor tube 14 contact the seventh cervical spine C7, the spinous process 512 of the first thoracic spine T1, and the occipital protuberance 520, and the sensor tube 14 does not fully fit the all cervical spines (the first through seventh cervical spines C1 through C7).

As a result, the distance between the spinal cord 511 and the sensor surfaces 15a of the magnetic sensors 15 facing the cervical spines increases. If the distance between the spinal cord 511 and the sensor surfaces 15a of the magnetic sensors 15 increases, the detection rate of weak signals propagated through the spinal cord 511 decreases greatly.

The center of the magnetic sensor array 16 is aligned with the fifth cervical spine C5 to obtain biomagnetism measurement data in a region around the fifth cervical spine C5 that is in the middle of the third through seventh cervical spines C3 thorough C7 where a lesion is often found.

In FIG. 6, the sensor tube 14 is inclined toward the subject with reference to the spinous process 512 of the seventh cervical spine C7. In other words, the sensor surface 15a of each of the magnetic sensors 15 is inclined with respect to the mount surface 11a of the inclination gantry 11 in the same direction as the inclined surface 11b of the inclination gantry 11 (inclination angle $\theta_2$). Properly inclining the sensor tube 14 (i.e., the sensor surfaces 15a of the magnetic sensors 15) makes it possible to minimize the influence of the seventh cervical spine C7, the spinous process 512 of the first thoracic spine T1, and the occipital protuberance 520, and thereby makes it possible to arrange the sensor surfaces 15a of the magnetic sensors 15 along a direction in which the spinal cord 511 extends.

In FIG. 6, the curvature of the sensor tube 14, which is positioned by aligning the center of the magnetic sensor array 16 with the fifth cervical spine C5, generally matches the curvature of the cervical region 510, and the sensor tube 14 far better fits the cervical region 510 compared with the configuration of FIG. 5. Accordingly, the overall distance between the spinal cord 511 and the sensor surfaces 15a of the magnetic sensors 15 facing the cervical spines is decreased. Because signals propagated through the spinal cord 511 are weak, the effect of reducing the distance between the spinal cord 511 and the sensor surfaces 15a of the magnetic sensors 15 is significant. Thus, compared with the configuration of FIG. 5, the configuration of FIG. 6 makes it possible to greatly improve the detection rate of weak signals propagated through the spinal cord 511.

COMPARATIVE EXAMPLES AND EXAMPLES

Comparative Example 1

In Comparative Example 1, measurement was conducted using a magnetic measuring apparatus 10x including the bed 21, the X-ray source 22, the X-ray photography film 23, and the electrical stimulation device 24. The cryocooling system 13 and the electrical stimulation device 24 were placed outside of a magnetically shielded room, and other components were placed in the magnetically shielded room. The magnetic measuring apparatus 10x is substantially the same as the magnetic measuring apparatus 10 except that the magnetic measuring apparatus 10x does not include the inclination gantry 11. That is, the bottom surface of the cryostat 12 of the magnetic measuring apparatus 10x is directly placed on a horizontal surface, and the inclination angle of the sensor surface 15a of each of the magnetic sensors 15 with respect to the horizontal surface is 0 degrees.

As illustrated in FIG. 4, the subject 500 was placed supine on the horizontal bed 21, and the curved surface 14a of the sensor tube 14 was brought into contact with the cervical region such that the center of the magnetic sensor array 16 was substantially aligned with the fifth cervical spine C5.

In this condition, X-ray images of 27 subjects (aged between 27 and 81) were taken, and the distance (which is hereafter referred to as a "distance L") between the vertebral body posterior wall of the fifth cervical spine C5 and the sensor end was measured for each of the subjects based on the X-ray images. The average distance L was 114.4 mm, the largest distance L was 146 mm, and the smallest distance L was 91 mm.

Also, biomagnetism measurement of the cervical region was conducted. Specifically, after carrying the X-ray source 22 and the X-ray photography film 23 out of the magnetically shielded room, the median nerve of a cubital region was electrically stimulated (with an electric current between 3 mA and 15 mA) by using Electromyography Evoked Potentials Inspector MEB-2306 of Nihon Kohden Corporation as the electrical stimulation device 24, and neural activity synchronized with the electric stimulation and being propagated through the nerve was measured at the cervical region based on output signals of the magnetic sensor array 16. Average data of 2000 measurements was obtained. Weak propagation signals were detected in 17 subjects out of 27 subjects, and the signal detection rate was 63.0%.

Example 1

X-ray photography and biomagnetism measurement of the cervical region were conducted in a manner similar to Comparative Example 1 except that the magnetic measuring apparatus 10 including the incline mount 11 was used instead of the magnetic measuring apparatus 10x that does not include the incline mount 11.

In Example 1, the inclination gantry 11 with an inclination angle $\theta_1$ of 5 degrees was used, and the inclination angle $\theta_2$ was set at 5 degrees. Because the upper surface of the bed 21 is horizontal (or parallel to the mount surface 11a), the inclination angle $\theta_2$ becomes equal to an angle (which is hereafter referred to as an angle $\theta_3$) formed between an examination region of the subject 500 and the sensor surfaces 15a of the magnetic sensors 15.

The average distance L was 107.1 mm, the largest distance L was 151 mm, and the smallest distance L was 93 mm. Thus, the distance L was significantly reduced compared with Comparative Example 1. Here, the significant reduction of the distance L indicates the significant reduction of the distance between the spinal cord 511 and the sensor surfaces 15a of the magnetic sensors 15 facing the cervical spines.

In the measurement at the cervical region using the magnetic measuring apparatus 10, weak propagation signals were detected in 22 subjects out of 27 subjects, and the signal detection rate was 81.5%. Thus, the detection rate was significantly improved compared with Comparative Example 1.

Example 2

X-ray photography and biomagnetism measurement of the cervical region were conducted in a manner similar to Example 1 except that the inclination angle $\theta_1$ was set at 10 degrees and the inclination angle $\theta_2$ was set at 10 degrees.

The average distance L was 103.1 mm, the largest distance L was 121 mm, and the smallest distance L was 87 mm. Thus, the distance L was further reduced compared with Example 1.

In the measurement at the cervical region using the magnetic measuring apparatus 10, weak propagation signals were detected in 25 subjects out of 27 subjects, and the signal detection rate was 92.6%. Thus, the signal detection rate exceeded 90% and significantly improved compared with Comparative Example 1.

Example 3

X-ray photography and biomagnetism measurement of the cervical region were conducted in a manner similar to Example 1 except that the inclination angle $\theta_1$ was set at 15 degrees and the inclination angle $\theta_2$ was set at 15 degrees.

The average distance L was 101.1 mm, the largest distance L was 120 mm, and the smallest distance L was 87 mm. Thus, the distance L measured in Example 3 did not differ greatly from that measured in Example 2.

In the measurement at the cervical region using the magnetic measuring apparatus 10, weak propagation signals were detected in 25 subjects out of 27 subjects, and the signal detection rate was 92.6%. Thus, the signal detection rate exceeded 90% and significantly improved compared with Comparative Example 1.

Example 4

X-ray photography and biomagnetism measurement of the cervical region were conducted in a manner similar to Example 1 except that the inclination angle $\theta_1$ was set at 20 degrees and the inclination angle $\theta_2$ was set at 20 degrees.

The average distance L was 100.1 mm, the largest distance L was 121 mm, and the smallest distance L was 85 mm. Thus, the distance L measured in Example 4 did not differ greatly from that measured in Examples 2 and 3.

In the measurement at the cervical region using the magnetic measuring apparatus 10, weak propagation signals were detected in 25 subjects out of 27 subjects, and the signal detection rate was 92.6%. Thus, the signal detection rate exceeded 90% and significantly improved compared with Comparative Example 1.

Example 5

X-ray photography and biomagnetism measurement of the cervical region were conducted in a manner similar to Example 1 except that the inclination angle $\theta_1$ was set at 25 degrees and the inclination angle $\theta_2$ was set at 25 degrees.

The average distance L was 100.7 mm, the largest distance L was 121 mm, and the smallest distance L was 84 mm. Thus, the distance L measured in Example 5 did not differ greatly from that measured in Examples 2, 3, and 4.

In the measurement at the cervical region using the magnetic measuring apparatus 10, weak propagation signals were detected in 19 subjects out of 27 subjects, and the signal detection rate was 70.4%. This indicates that the subject 500 needed to take an unnatural posture due to the large inclination and could not maintain the posture during the measurement; and as a result, the distance between the subject 500 and the sensor surfaces 15a of the magnetic sensors 15 increased and the magnetic sensors 15 became unable to detect signals.

Example 6

The inclination angle $\theta_1$ was set at 25 degrees and the inclination angle $\theta_2$ was set at 25 degrees. Then, by using the inclination adjusting mechanism of the bed 21, the inclination angle of the bed 21 was adjusted in a direction to reduce the inclination by 5 degrees (in a direction to lift the head side of the subject 500) to set the angle $\theta_3$ at 20 degrees. Except for these conditions, X-ray photography and biomagnetism measurement of the cervical region were conducted in a manner similar to Example 1.

The average distance L was 100.7 mm, the largest distance L was 124 mm, and the smallest distance L was 86 mm. Thus, the distance L measured in Example 6 did not differ greatly from that measured in Examples 2, 3, and 4.

In the measurement at the cervical region using the magnetic measuring apparatus 10, weak propagation signals were detected in 25 subjects out of 27 subjects, and the signal detection rate was 92.6%. Thus, the detection rate was substantially the same as that in Example 4.

Comparative Example 2

The subject 500 was placed supine on the horizontal bed 21, and the curved surface 14a of the sensor tube 14 was brought into contact with the lumbar region such that the center of the magnetic sensor array 16 was substantially aligned with the fifth lumbar spine. Except for these conditions, biomagnetism measurement was conducted in a manner similar to Comparative Example 1.

In the biomagnetism measurement, neural activity synchronized with the electric stimulation and being propagated through the nerve was measured at the lumbar region by using the magnetic measuring apparatus 10x. Average data of 2000 measurements was obtained. Weak propagation signals were detected in 12 subjects out of 26 subjects, and the signal detection rate was 46.2%.

Example 7

X-ray photography and biomagnetism measurement of the lumbar region were conducted in a manner similar to Comparative Example 2 except that the inclination angle $\theta_1$ was set at 5 degrees and the inclination angle $\theta_2$ was set at 5 degrees.

In the measurement at the lumbar region using the magnetic measuring apparatus 10, weak propagation signals were detected in 18 subjects out of 26 subjects, and the signal detection rate was 69.2%. Thus, the detection rate was significantly improved compared with Comparative Example 2.

Example 8

X-ray photography and biomagnetism measurement of the lumbar region were conducted in a manner similar to Example 7 except that the inclination angle $\theta_1$ was set at 10 degrees and the inclination angle $\theta_2$ was set at 10 degrees.

In the measurement at the lumbar region using the magnetic measuring apparatus 10, weak propagation signals were detected in 22 subjects out of 26 subjects, and the signal detection rate was 84.6%. Thus, the signal detection rate exceeded 80% and significantly improved compared with Comparative Example 2.

Example 9

X-ray photography and biomagnetism measurement of the lumbar region were conducted in a manner similar to Example 7 except that the inclination angle $\theta_1$ was set at 15 degrees and the inclination angle $\theta_2$ was set at 15 degrees.

In the measurement at the lumbar region using the magnetic measuring apparatus 10, weak propagation signals were detected in 23 subjects out of 26 subjects, and the signal detection rate was 88.5%. Thus, the signal detection rate exceeded 80% and significantly improved compared with Comparative Example 2.

Example 10

X-ray photography and biomagnetism measurement of the lumbar region were conducted in a manner similar to Example 7 except that the inclination angle $\theta_1$ was set at 20 degrees and the inclination angle $\theta_2$ was set at 20 degrees.

In the measurement at the lumbar region using the magnetic measuring apparatus 10, weak propagation signals were detected in 22 subjects out of 26 subjects, and the signal detection rate was 84.6%. Thus, the signal detection rate exceeded 80% and significantly improved compared with Comparative Example 2.

Example 11

X-ray photography and biomagnetism measurement of the lumbar region were conducted in a manner similar to Example 7 except that the inclination angle $\theta_1$ was set at 25 degrees and the inclination angle $\theta_2$ was set at 25 degrees.

In the measurement at the lumbar region using the magnetic measuring apparatus 10, weak propagation signals were detected in 18 subjects out of 26 subjects, and the signal detection rate was 69.2%. This indicates that the subject 500 needed to take an unnatural posture due to the large inclination and could not maintain the posture during the measurement; and as a result, the distance between the subject 500 and the sensor surfaces 15a of the magnetic sensors 15 increased and the magnetic sensors 15 became unable to detect signals.

SUMMARY

The results of Comparative Examples and Examples are provided in Table 1 below.

TABLE 1

|  | Examination Region | Inclination Angle $\theta_1$ | Angle $\theta_3$ | No. of Subjects | Detection Count | Detection rate |
|---|---|---|---|---|---|---|
| Comparative Example 1 | Cervical region | — | 0° | 27 | 17 | 63.0% |
| Example 1 | Cervical region | 5° | 5° | 27 | 22 | 81.5% |
| Example 2 | Cervical region | 10° | 10° | 27 | 25 | 92.6% |
| Example 3 | Cervical region | 15° | 15° | 27 | 25 | 92.6% |
| Example 4 | Cervical region | 20° | 20° | 27 | 25 | 92.6% |

TABLE 1-continued

|  | Examination Region | Inclination Angle $\theta_1$ | Angle $\theta_3$ | No. of Subjects | Detection Count | Detection rate |
|---|---|---|---|---|---|---|
| Example 5 | Cervical region | 25° | 25° | 27 | 19 | 70.4% |
| Example 6 | Cervical region | 25° | 20° | 27 | 25 | 92.6% |
| Comparative Example 2 | Lumbar region | — | 0° | 26 | 12 | 46.2% |
| Example 7 | Lumbar region | 5° | 5° | 26 | 18 | 69.2% |
| Example 8 | Lumbar region | 10° | 10° | 26 | 22 | 84.6% |
| Example 9 | Lumbar region | 15° | 15° | 26 | 23 | 88.5% |
| Example 10 | Lumbar region | 20° | 20° | 26 | 22 | 84.6% |
| Example 11 | Lumbar region | 25° | 25° | 26 | 18 | 69.2% |

As indicated by Table 1, regardless of whether the examination region is the cervical region or the lumbar region, the signal detection rate is improved in cases where the angle $\theta_3$ is greater than or equal to 10 degrees and less than or equal to 20 degrees.

Here, the cases where the angle $\theta_3$ is greater than or equal to 10 degrees and less than or equal to 20 degrees correspond to cases where the inclination angle $\theta_2$ is greater than or equal to 10 degrees and less than or equal to 20 degrees and the bed 21 is horizontal. Also, there are cases where the inclination angle $\theta_2$ is greater than 20 degrees but the angle $\theta_3$ is adjusted by the inclination adjusting mechanism of the bed 21 to become greater than or equal to 10 degrees and less than or equal to 20 degrees.

A magnetic measuring apparatus according to embodiments of the present invention are described above. However, the present invention is not limited to the specifically disclosed embodiments, and variations and modifications may be made without departing from the scope of the present invention.

For example, a magnetic measuring apparatus of the present invention is not limited to a magnetospinograph that detects an electric current flowing through the spinal cord as a magnetic field. For example, a magnetic measuring apparatus of the present invention may be used for a magnetoencephalograph or a magnetocardiograph.

When flat magnetic sensors, which are short in a direction orthogonal to their sensor surfaces, are used, it is not always necessary to incline the sensor surfaces of all the magnetic sensors in the same direction. For example, each magnetic sensor may be disposed to extend along the inner curved surface. In this case, for example, a magnetic measuring apparatus may be designed such that the inclination angle between the sensor surface of a center magnetic sensor, which is disposed in the middle in the y direction, and the mount surface of the inclination gantry becomes equal to the inclination angle between the inclined surface of the inclination gantry and the mount surface.

What is claimed is:

1. A magnetic measuring apparatus, comprising:
an inclination gantry including a mount surface and an inclined surface that is inclined with respect to the mount surface;
a cryostat disposed on the inclined surface;
a cryocooling system connected to the cryostat;
a sensor tube connected to the cryostat and including a curved surface that does not curve in a predetermined direction and curves in a direction orthogonal to the predetermined direction such that a center of the curved surface protrudes with respect to side edges of the curved surface; and
a magnetic sensor that measures biomagnetism, the magnetic sensor being housed in the sensor tube such that a sensor surface of the magnetic sensor faces the curved surface,
wherein the sensor surface is inclined with respect to the mount surface in a direction that is same as a direction in which the inclined surface is inclined.

2. The magnetic measuring apparatus as claimed in claim 1, wherein an inclination angle of the sensor surface with respect to the mount surface is equal to an inclination angle of the inclined surface with respect to the mount surface.

3. The magnetic measuring apparatus as claimed in claim 1, wherein
the magnetic sensor comprises multiple magnetic sensors that measure biomagnetism, the magnetic sensors being housed in the sensor tube such that the sensor surface of each of the magnetic sensors faces the curved surface; and
the sensor surface of each of the magnetic sensors is inclined with respect to the mount surface in the direction that is the same as the direction in which the inclined surface is inclined.

4. The magnetic measuring apparatus as claimed in claim 3, wherein an inclination angle of the sensor surface of each of the magnetic sensors with respect to the mount surface is equal to an inclination angle of the inclined surface with respect to the mount surface.

5. The magnetic measuring apparatus as claimed in claim 3, wherein the sensor surface of one of the magnetic sensors whose position in the sensor tube is closer to the center of the curved surface in the direction orthogonal to the predetermined direction protrudes more toward the curved surface compared with the sensor surface of another one of the magnetic sensors that is positioned closer to one of the side edges of the curved surface.

6. The magnetic measuring apparatus as claimed in claim 2, wherein the inclination angles are greater than or equal to 10 degrees and less than or equal to 20 degrees.

7. The magnetic measuring apparatus as claimed in claim 1, wherein an inclination angle of the sensor surface with respect to the mount surface is fixed.

8. The magnetic measuring apparatus as claimed in claim 1, further comprising:
an X-ray photography unit that takes an X-ray photograph of a space including a space above the curved surface; and
an electrical stimulation device that percutaneously applies an electric current to a subject to stimulate a target nerve.

9. The magnetic measuring apparatus as claimed in claim 8, wherein the magnetic sensor measures propagation of neural activity that is synchronized with the stimulation.

10. The magnetic measuring apparatus as claimed in claim 1, further comprising:
- a bed on which a subject is laid down such that an examination region of the subject contacts the curved surface,
- wherein the bed includes an inclination adjusting mechanism configured to adjust an angle of the bed in a direction to reduce an angle of the examination region with respect to the sensor surface.

* * * * *